(12) United States Patent
Kleyman

(10) Patent No.: US 9,381,333 B2
(45) Date of Patent: *Jul. 5, 2016

(54) SURGICAL DEVICE HAVING INDICIA FOR CUTTING TO SIZE

(71) Applicant: Covidien LP, Mansfield, MA (US)

(72) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/766,961

(22) Filed: Feb. 14, 2013

(65) Prior Publication Data

US 2013/0226216 A1 Aug. 29, 2013

Related U.S. Application Data

(63) Continuation of application No. 12/813,800, filed on Jun. 11, 2010, now Pat. No. 8,398,667.

(60) Provisional application No. 61/231,798, filed on Aug. 6, 2009.

(51) Int. Cl.
*A61M 29/02* (2006.01)
*A61B 17/34* (2006.01)
*A61M 29/00* (2006.01)

(52) U.S. Cl.
CPC ............ *A61M 29/02* (2013.01); *A61B 17/3423* (2013.01); *A61M 29/00* (2013.01); *A61B 17/3431* (2013.01); *A61B 2017/3441* (2013.01); *A61B 2017/3445* (2013.01)

(58) Field of Classification Search
CPC .................. A61B 17/12022; A61B 17/0057; A61B 17/3423; A61B 2017/3445; A61M 29/02; A61M 29/00

USPC ............................ 606/185, 186, 191; 600/206
See application file for complete search history.

(56) References Cited

U.S. PATENT DOCUMENTS 5,269,772 A 12/1993 Wilk
5,375,588 A 12/1994 Yoon
6,454,783 B1 9/2002 Piskun
(Continued)

FOREIGN PATENT DOCUMENTS

EP 2044889 4/2009
WO WO 01/49363 7/2001

OTHER PUBLICATIONS

European Search Report for corresponding EP 10 25 1397, date of completion is Sep. 30, 2010 (3 pages).

*Primary Examiner* — Victor Nguyen

(57) ABSTRACT

A surgical apparatus includes a seal anchor member including a compressible material. The seal anchor member may be adapted to transition between a first condition for insertion of at least a portion of the seal anchor member within a tissue tract and a second condition to facilitate a securing of the seal anchor member within a tissue tract and in substantial sealed relation with tissue surfaces defining a tissue tract. The seal anchor member may define at least one port extending between the proximal and distal ends, the at least one port being adapted for the reception of an object whereby compressible material defining the at least one port is adapted to deform to establish a substantial scaled relation with the object. The seal anchor member may include indicia that indicates to a user a location at which the member may be cut to reduce the size of the member.

10 Claims, 8 Drawing Sheets

(56) References Cited

U.S. PATENT DOCUMENTS

| | | |
|---|---|---|
| 7,344,547 B2 | 3/2008 | Piskun |
| 8,398,667 B2 * | 3/2013 | Kleyman .................. 606/191 |
| 2006/0247673 A1 | 11/2006 | Voegele et al. |
| 2006/0270911 A1 | 11/2006 | Voegele et al. |
| 2009/0093752 A1 * | 4/2009 | Richard et al. .................. 604/24 |
| 2009/0187079 A1 * | 7/2009 | Albrecht et al. .............. 600/206 |

* cited by examiner

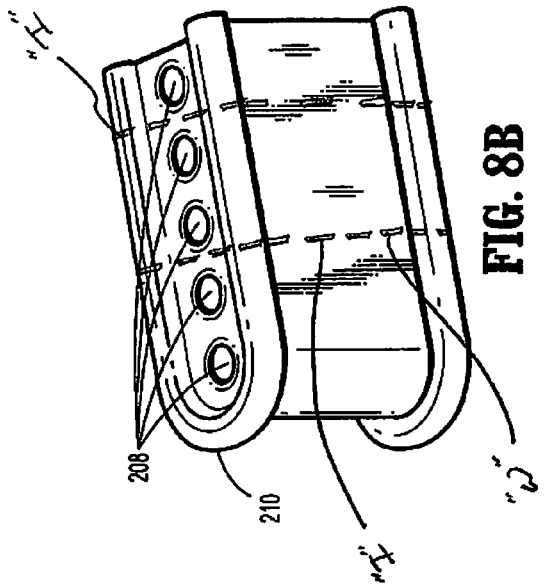
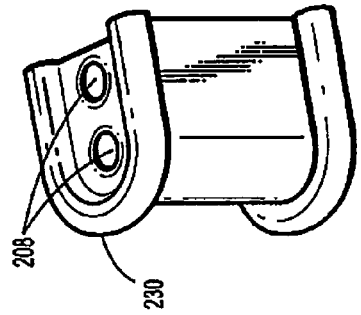
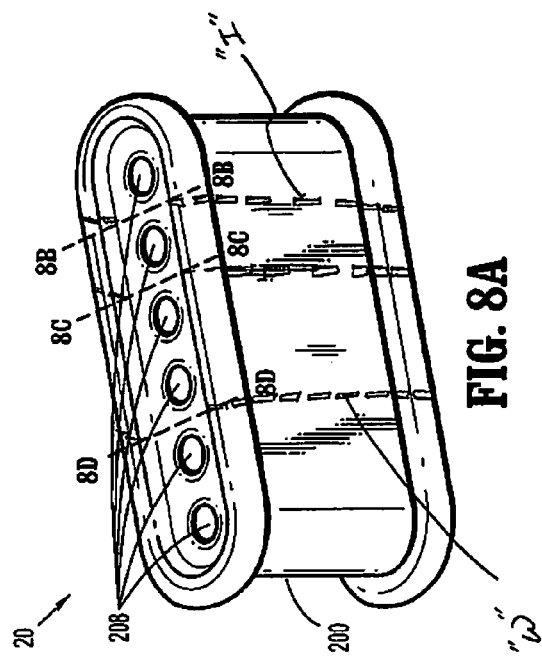
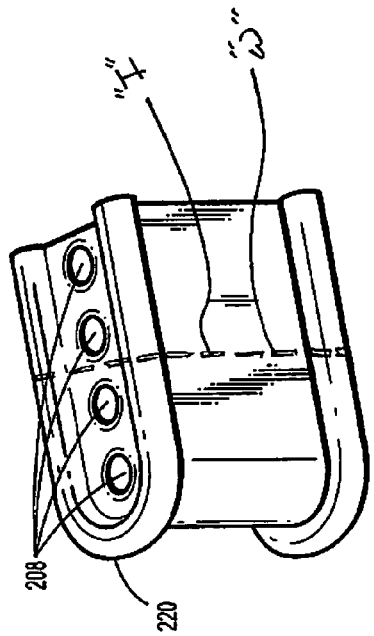

SURGICAL DEVICE HAVING INDICIA FOR CUTTING TO SIZE

CROSS REFERENCE TO RELATED APPLICATION

The present application is a continuation of U.S. patent application Ser. No. 12/813,800, filed on Jun. 11, 2010, which claims the benefit of and priority to U.S. Provisional Application Ser. No. 61/231,798 filed on Aug. 6, 2009, the entire contents of each of which are incorporated herein by reference.

BACKGROUND

1. Technical Field

The present disclosure relates to a seal for use in a surgical procedure. More particularly, the present disclosure relates to a seal anchor member adapted for insertion into an incision in tissue, and, for the sealed reception of one or more surgical objects such that a substantially fluid-tight seal is formed with both the tissue and the surgical object, or objects.

2. Background of the Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass, e.g., endoscopic, laparoscopic, arthroscopic, thoracic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to inhibit the escape of the insufflation gases and the deflation or collapse of the enlarged surgical site.

To this end, various valves and seals are used during the course of minimally invasive procedures and are widely known in the art. However, a continuing need exists for a seal anchor member that can be inserted directly into an incision in tissue in a narrow area, such as a cavity between two ribs, and that can accommodate a variety of surgical objects while maintaining the integrity of an insufflated workspace.

SUMMARY

According to an embodiment of the present invention, there is provided a surgical apparatus for positioning within a tissue tract accessing an underlying body cavity includes a seal anchor member comprising a compressible material and being adapted to transition between a first expanded condition and a second compressed condition. The first expanded condition facilitates a securing of the seal anchor member within the tissue tract and in substantial scaled relation with tissue surfaces defining the tissue tract, and the second compressed condition facilitates an at least partial insertion of the seal anchor member within the tissue tract. The seal anchor member may be formed of a foam material, which may be at least partially constituted of a material selected from the group consisting of polyisoprene, urethane, and silicone. Alternatively, the seal anchor member may be formed of a gel material.

The seal anchor member includes proximal and distal ends that define elongated, e.g., oval or oblong, perimeters to facilitate the positioning of the seal anchor member within a tissue tract accessing an underlying body cavity. At least one of the proximal and distal ends of the seal anchor member may exhibit an arcuate configuration, which may be either concave or convex. The seal anchor member may be rolled, twisted, or otherwise deformed to fit nonlinearly into the tissue tract. The seal anchor member may also be cut to better suit a surgical procedure.

At least one port extends between the proximal and distal ends and is adapted for the reception of an object whereby compressible material defining the at least one port is adapted to deform to establish a substantial sealed relation with the object. The at least one port may contain at least an undercut to protect against fluid leaks. The seal anchor member may include a plurality of ports that may be configured linearly with respect to the major diameter of the perimeter of at least one of the distal and proximal ends. Each port may be spaced equally from its neighboring ports.

According to an embodiment of the present invention, there is provided a surgical apparatus for positioning within a tissue tract accessing an underlying body cavity, which comprises: a seal anchor member comprising a compressible material. The seal anchor member may be adapted to transition between a first condition for insertion of at least a portion of the seal anchor member within a tissue tract and a second condition to facilitate a securing of the seal anchor member within a tissue tract and in substantial sealed relation with tissue surfaces defining a tissue tract. The seal anchor member may have proximal and distal ends and define at least one port extending between the proximal and distal ends, the at least one port being adapted for the reception of an object whereby compressible material defining the at least one port is adapted to deform to establish a substantial sealed relation with the object. The seal anchor member may have a non-circular cross-section.

The seal anchor member may be formed of a foam material. The foam material may be at least partially constituted of a material selected from the group consisting of polyisoprene, urethane, and silicone. The seal anchor member may also be formed of a gel material. The at least one port may include at least one undercut to reduce the likelihood of leaks therethrough. Also, the surgical apparatus may include indicia that indicates to a user a location at which the apparatus may be cut. The seal anchor member may include a plurality of ports, and the plurality of ports may be configured linearly with respect to each other. Each port of the plurality of ports may be spaced equally from its neighboring ports. In use, the seal anchor member may have an initial expanded condition, and may be adapted to be compressed by an external compressing force from the initial expanded condition to the first condition to facilitate insertion of at least a portion of the seal anchor member within a tissue tract, the anchor seal member being further adapted upon removal of the compressing force to expand towards its initial expanded condition and to its second condition to facilitate a securing of the seal anchor member within a tissue tract and in substantial sealed relation with tissue surfaces defining a tissue tract.

According to another embodiment of the present invention, there is provided a surgical apparatus for positioning within a tissue tract accessing an underlying body cavity, which comprises: a seal anchor member comprising a compressible material; the seal anchor member being adapted to transition between a first condition for insertion of at least a portion of the seal anchor member within a tissue tract and a second condition to facilitate a securing of the seal anchor member within a tissue tract and in substantial sealed relation with tissue surfaces defining a tissue tract, the seal anchor member having proximal and distal ends and defining a plurality of ports extending between the proximal and distal ends, at least one of the plurality of ports being adapted for the reception of an object whereby compressible material defining the at least one port is adapted to deform to establish a substantial sealed relation with the object, wherein the plurality of ports are arranged linearly relative to each other.

The seal anchor member may be formed of a foam material. The foam material may be at least partially constituted of a material selected from the group consisting of polyisoprene, urethane, and silicone. The seal anchor member may also be formed of a gel material. The port may include at least one undercut to reduce the likelihood of leaks therethrough. The surgical apparatus may include indicia that indicates to a user a location at which the apparatus may be cut. The seal anchor member may have a non-circular cross-section. Each port may be spaced equally from its adjacent ports. In use, the seal anchor member may have an initial expanded condition, and may be adapted to be compressed by an external compressing force from the initial expanded condition to the first condition to facilitate insertion of at least a portion of the seal anchor member within a tissue tract, the anchor seal member being further adapted upon removal of the compressing force to expand towards its initial expanded condition and to its second condition to facilitate a securing of the seal anchor member within a tissue tract and in substantial scaled relation with tissue surfaces defining a tissue tract.

According to still another embodiment of the present invention, there is provided a surgical apparatus for positioning within a tissue tract accessing an underlying body cavity, which comprises: a seal anchor member comprising a compressible material; the seal anchor member being adapted to transition between a first condition for insertion of at least a portion of the seal anchor member within a tissue tract and a second condition to facilitate a securing of the seal anchor member within a tissue tract and in substantial sealed relation with tissue surfaces defining a tissue tract, the seal anchor member having proximal and distal ends and defining at least one port extending between the proximal and distal ends, the at least one port being adapted for the reception of an object whereby compressible material defining the at least one port is adapted to deform to establish a substantial sealed relation with the object, and wherein the at least one port includes an undercut to reduce the likelihood of leaks therethrough.

According to still another embodiment of the present invention, there is provided a seal anchor member being configured and dimensioned to be compressed for insertion into an incision and, once inserted, to expand so as to be secured within and seal against the incision, the seal anchor member defining at least one port extending generally longitudinally and being adapted for sealed reception of a surgical object, the seal anchor member having indicia and being formed from a material suitable to be cut along the indicia by, e.g., a surgeon's scalpel. The indicia may be located at positions such that, when the seal anchor member is separated, e.g., cut, along the indicia, the seal anchor member has a cross-sectional shape that is different from the original cross-sectional shape of the anchor seal member. The indicia may be one of lines or markings on a surface of the seal anchor member. Coincident with the indicia, the seal anchor member may also include an area of weakening to ease the cutting of the seal anchor member. The area of weakening may include a perforation and/or a slit.

According to still another embodiment of the present invention, there is provided a seal anchor member being configured and dimensioned to be compressed for insertion into an incision and, once inserted, to expand so as to be secured within and seal against the incision, the seal anchor member defining at least one port extending generally longitudinally and being adapted for sealed reception of a surgical object, the seal anchor member having indicia that indicate to a user a position on the seal anchor member of an area of weakening, the area of weakening enabling the seal anchor member to be reduced in size. The area of weakening may be one of a perforation or a slit. The seal anchor member may include a plurality of ports, the indicia indicating a position at which, when the scat anchor member is separated at the indicia, the number of ports of the seal anchor member is reduced. Alternatively, the indicia may indicate a position at which, when the seal anchor member is separated at the indicia, the seal anchor member is reduced in size so as to be accommodated in a relatively smaller incision without reducing the number of ports.

BRIEF DESCRIPTION OF THE DRAWINGS

Various embodiments of the present disclosure are described hereinbelow with references to the drawings, wherein:

FIGS. 8A-8D are perspective views of a surgical apparatus in accordance with another embodiment of the present disclosure illustrating a seal anchor member cut to varying lengths.

DETAILED DESCRIPTION OF THE EMBODIMENTS

Figure 1:
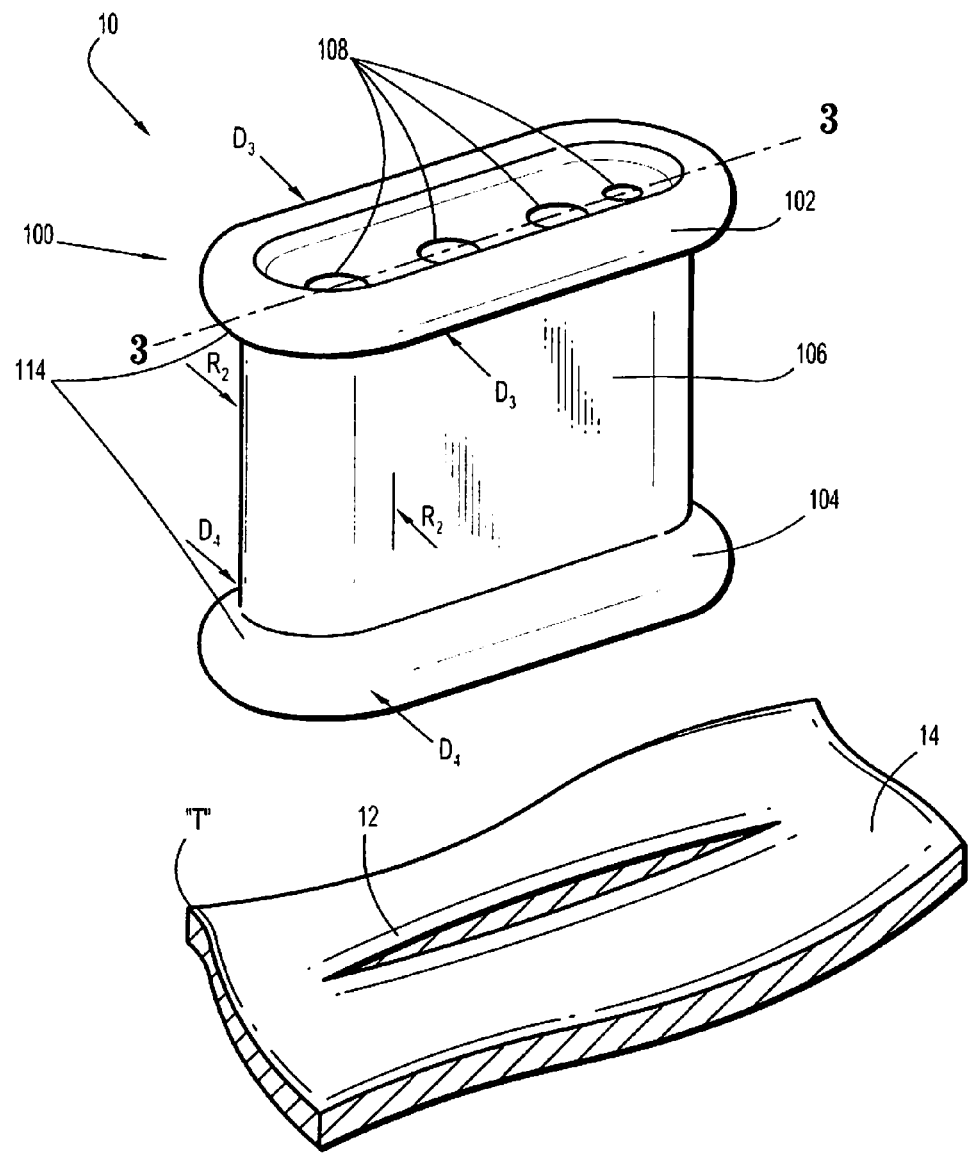
FIG. 1 is a top, perspective view of a surgical apparatus in accordance with the principles of the present disclosure shown in an expanded condition illustrating a seal anchor member positioned relative to the tissue.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

With reference to FIGS. 1-4, a surgical apparatus 10 for use in a surgical procedure, e.g., a minimally invasive procedure is illustrated. Surgical apparatus 10 includes seal anchor member 100 having proximal end 102 and distal end 104.

Seal anchor member 100 includes one or more ports 108, i.e., lumen, that extend through seal anchor member 100 between proximal end 102 and distal end 104.

Seal anchor member 100 is formed from a suitable foam material having sufficient compliance to form a seal about one or more surgical objects, shown generally as surgical object "I" (FIG. 4), and also establish a sealing relation with tissue "T". The foam is sufficiently compliant to accommodate motion of the surgical object "I". In one embodiment, the foam includes a polyisoprene material. An example of an anchor member formed of, e.g., foam, is disclosed in applicant's co-pending U.S. patent application Ser. No. 12/244,024, filed Oct. 2, 2008, the entire contents of which are hereby incorporated by reference herein.

Figure 2:
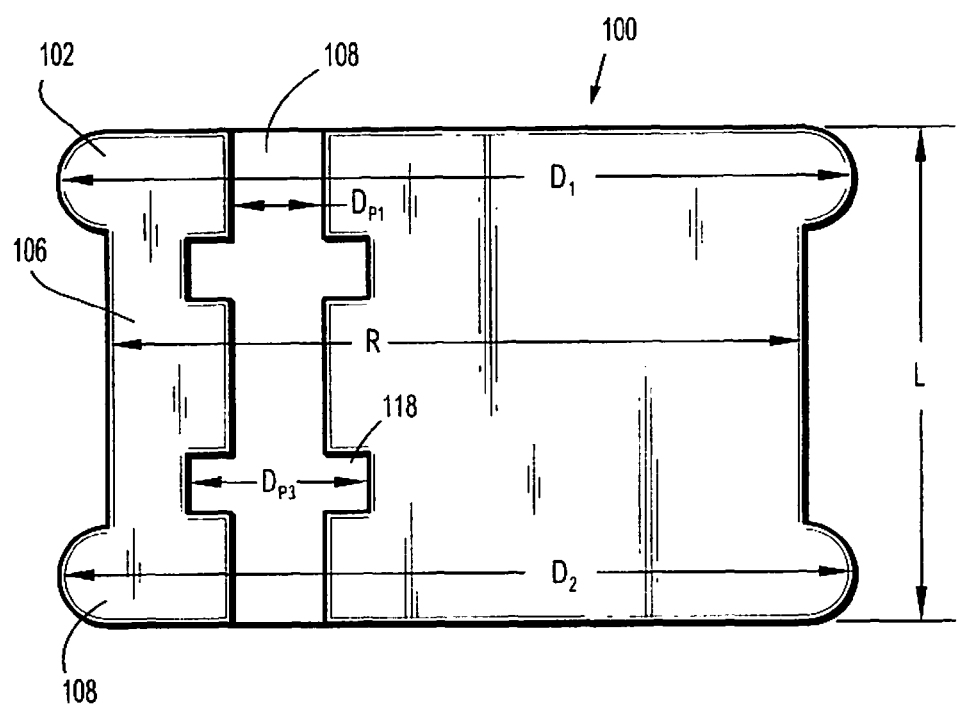
FIG. 2 is a side, schematic view of the seal anchor member of FIG. 1.
Figure 3:
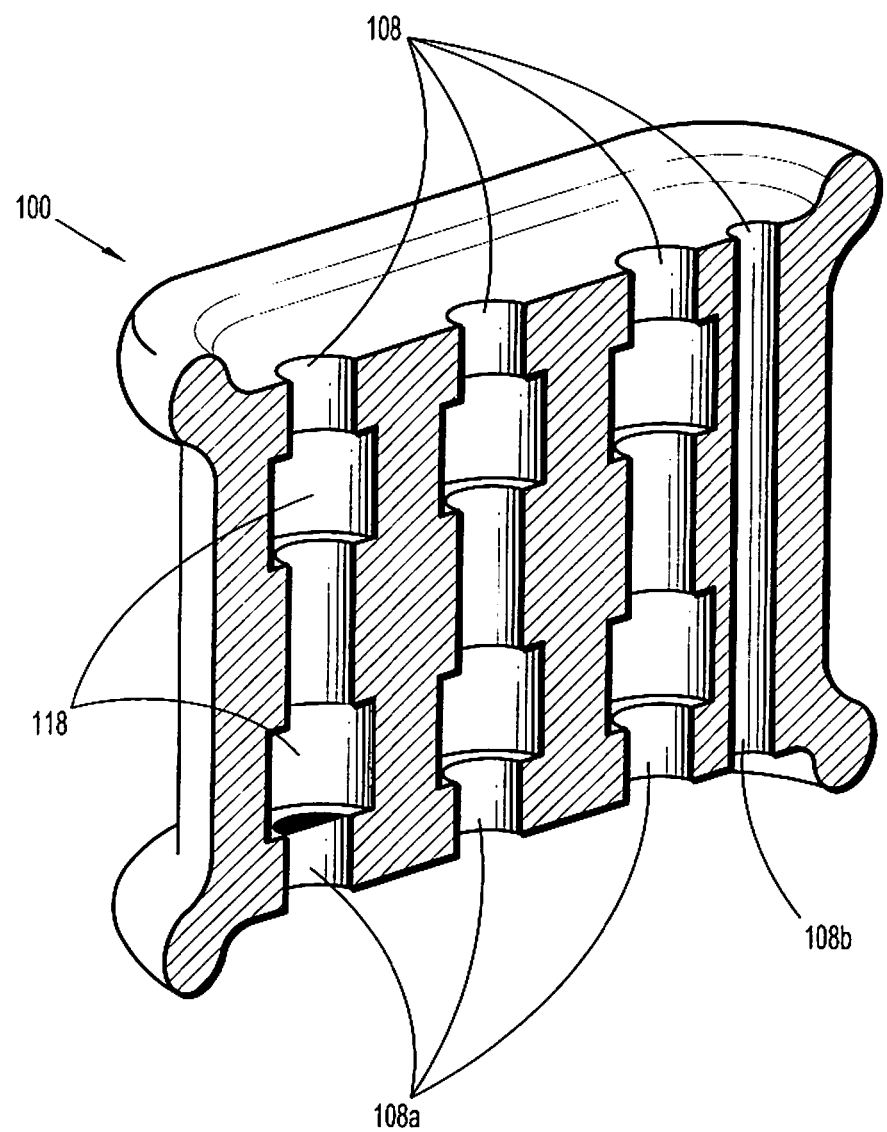
FIG. 3 is a cross-sectional view of the seal anchor member of FIG. 1 taken along section line 3-3 of FIG. 1 illustrating a plurality of ports defining undercuts.

Proximal end 102 of seal anchor member 100 defines a first major diameter $D_1$ and distal end 104 defines a second major diameter $D_2$. In an embodiment of seal anchor member 100, the respective first and second major diameters $D_1$, $D_2$ of the proximal and distal ends 102, 104 are substantially equivalent, as seen in FIG. 2, although an embodiment of seal anchor member 100 in which diameters $D_1$, $D_2$ are different is also within the scope of the present disclosure. Also, proximal end 102 of seal anchor member 100 defines a first minor diameter $D_3$ distal end 104 defines a second minor diameter $D_4$. In an embodiment of seal anchor member 100, the respective first and second minor diameters $D_3$, $D_4$ of the proximal and distal ends 102, 104 are substantially equivalent, as seen in FIG. 2, although an embodiment of seal anchor member 100 in which diameters $D_3$, $D_4$ are different is also within the scope of the present disclosure. Advantageously, first and second major diameters $D_1$, $D_2$ of the proximal and distal ends 102, 104 are greater than first and second minor diameters $D_3$, $D_4$ of the proximal and distal ends 102, 104, such that the seal anchor member 100 has, in cross-section, a non-circular, e.g., oblong, oval, race-track, etc., shape.

As depicted in FIG. 1, positioning members 114 of proximal and distal ends 102, 104 may define arcuate surfaces to assist in the insertion of seal anchor member 100 within a tissue tract 12 defined by tissue surfaces 14 and formed in tissue "T", e.g., an incision, as discussed in further detail below. Alternatively, proximal and distal ends 102,104 may define substantially planar surfaces or substantially arcuate surfaces. Embodiments are contemplated herein in which either or both of proximal and distal ends 102, 104 define surfaces that are either or both arcuate or planar. The arcuate surfaces may be either or both concave or convex.

Intermediate portion 106 extends between proximal and distal ends 102, 104 to define a dimension, or length, "L" therealong. Intermediate portion 106 further defines an intermediate major diameter "R" substantially parallel to major diameters $D_1$, $D_2$. The dimension "R" of intermediate portion 106 may remain substantially uniform along the dimension "L" thereof. Alternatively, the dimension "R" of intermediate portion 106 may vary along the dimension, or length, "L" thereof, thereby defining a cross-sectional dimension that varies along its length "L", which facilitates the anchoring of seal anchor member 100 within tissue "T". In addition, intermediate portion 106 may further define an intermediate minor diameter "$R_2$" substantially perpendicular to major diameter R. Advantageously, the intermediate minor diameter "$R_2$" being smaller than the major diameter R, such that the seal anchor member 100 has, in cross-section, a non-circular, e.g., oblong, oval, race-track, etc., shape.

The dimension "R" of intermediate portion 106 may be appreciably less than the respective major axes $D_1$, $D_2$ of proximal and distal ends 102, 104 to assist in anchoring seal anchor member 100 within tissue "T", as discussed in further detail below. However, in an alternate embodiment, the dimension "R" of intermediate portion 106 may be substantially equivalent to the respective major axes $D_1$, $D_2$ of proximal and distal ends 102, 104. In cross section, intermediate portion 106 may exhibit any suitable elongated configuration, e.g., substantially oval or oblong, for insertion into a narrow incision.

Each port 108 is configured to removably receive the surgical object "I". Prior to the insertion of surgical object "I", port 108 is in a first state in which port 108 defines a first or initial dimension $D_{P1}$. Port 108 may define an opening within seal anchor member 100 having an initial open state. Alternatively, $D_{P1}$ may be about 0 mm such that the escape of insufflation gas (not shown) through port 108 of seal anchor member 100 in the absence of surgical object "I" is substantially inhibited. For example, port 108 may be a slit extending the length "L" of seal anchor member 100 through proximal and distal ends 102, 104.

Upon the introduction of surgical object "I", port 108 transitions to a second state in which port 108 defines a second, larger dimension $D_{P2}$ that substantially approximates the diameter $D_1$ of surgical object "I" such that a substantially fluid-light seal is formed therewith, thereby substantially inhibiting the escape of insufflation gas (not shown) through port 108 of seal anchor member 100 in the presence of surgical object "I". $D_1$, and thus $D_{P2}$, will generally lie within the range of about 5 mm to about 12 mm, as these dimensions are typical of the surgical objects used during the course of minimally invasive procedures. However, a seal anchor member 100 including a port 108 that is capable of exhibiting substantially larger, or smaller dimensions in the second slate thereof is not beyond the scope of the present disclosure. Seal anchor member 100 may include a plurality of generally tubular port segments (not shown) defining ports 108. In addition, seal anchor 100 may be devoid of ports 108. With this arrangement, ports 108 are created within seal anchor member 100 during the insertion of the surgical object "I". In accordance with this embodiment, seal anchor member 100 is formed of a flowable or sufficiently compliant material such as a foam material, e.g., an open-cell polyurethane foam, or a gel.

Ports 108 may include ports 108a, which contain at least one undercut 118 that collects insufflation gas that leaks through the substantially fluid-tight seal between a surgical instrument "I" and a port 108a. Each undercut 118 defines a diameter $D_{P3}$ greater than $D_{P2}$ and a length along a port 108a less than "L". Insufflation gas that leaks through a substantially fluid-tight seal between an instrument "I" and a port 108a may collect in an undercut 118 to inhibit further leakage of the gas through the substantially fluid-tight seal. Furthermore, the undercuts 118 provide edges (where the respective diameters $D_{P1}$ of the lumen 108 transition to the diameters $D_{P3}$ of the undercut 118) that engage the outer surfaces of the instruments "I" inserted therethrough to further reduce leakage. Ports 108 may also include ports 108b, which do not contain undercuts 118, or any combination of ports 108a and ports 108b.

Generally, ports 108 are arranged linearly with respect to major diameter $D_1$. Ports 108 may alternatively be arranged linearly with respect to major diameter $D_2$ or dimension "R". However, embodiments in which ports 108 are arranged non-linearly, e.g., an oval or zigzag pattern, are also within the scope of this disclosure. Each port 108 may be spaced equally from its neighboring ports. However, embodiments in which ports 108 are spaced unequally are also within the scope of this disclosure.

Figure 5:
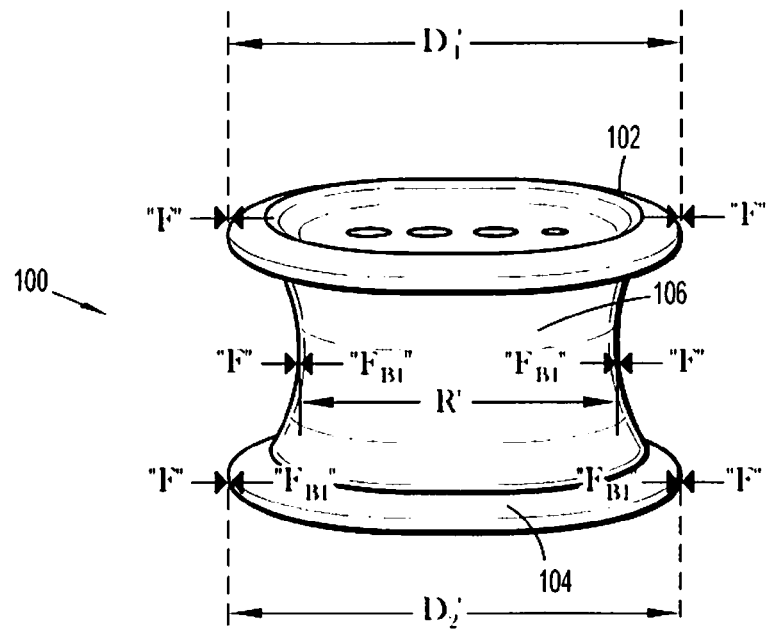
FIG. 5 is a perspective, schematic view of the seal anchor member of FIG. 1 shown in a compressed condition prior to the insertion thereof into an incision in tissue.
Figure 5:
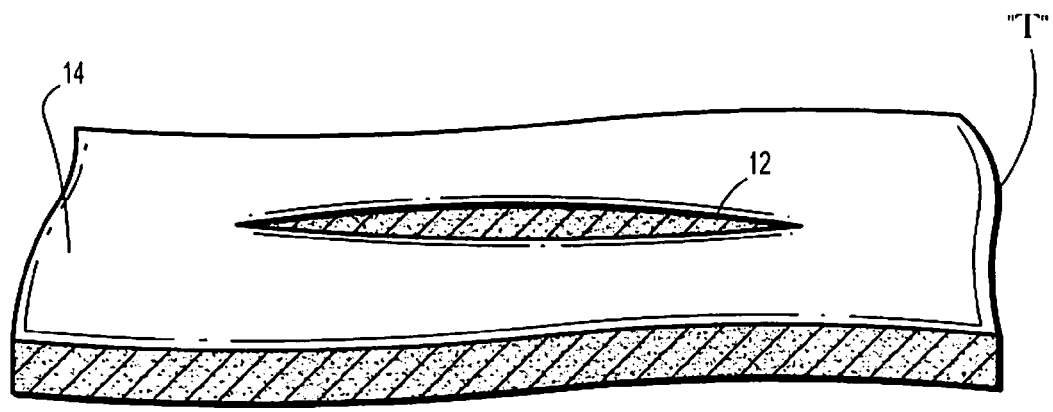

Referring now to FIGS. 1 and 5, seal anchor member 100 is adapted to transition from an expanded condition (FIG. 1) to a compressed condition (FIG. 5) so as to facilitate the insertion and securement thereof within tissue tract 12 in tissue "T". In the expanded condition, seal anchor member 100 is at rest and the respective major axes $D_1$, $D_2$ of the proximal and distal ends 102, 104 of seal anchor member 100, as well as the dimension "R" of the intermediate portion 106 are such that the seal anchor member 100 cannot be inserted within tissue tract 12. However, as seen in FIG. 5, in the compressed condition, proximal and distal ends 102, 104 of seal anchor member 100 as well as intermediate portion 106 are dimensioned for insertion into tissue tract 12.

Seal anchor member 100 is formed of a biocompatible compressible material that facilitates the resilient, reciprocal transitioning of seal anchor member 100 between the expanded and compressed conditions thereof. In one embodiment, the compressible material is a "memory" foam. An external force "F" is applied to seal anchor member 100 to cause the seal anchor member 100 to assume the compressed condition. External force "F" is directed inwardly and when seal anchor member 100 is subjected thereto, e.g., when seal anchor member 100 is squeezed, seal anchor member 100 undergoes an appreciable measure of deformation, thereby transitioning into the compressed condition.

As depicted in FIG. 5, as seal anchor member 100 is compressed under the influence of external force "F", an internal biasing force "$F_{B1}$" is created within seal anchor member 100 that is directed outwardly, opposing force "F". Internal biasing force "$F_{B1}$" endeavors to expand seal anchor member 100 and thereby return seal anchor member 100 towards the expanded condition thereof. Accordingly, as long as seal anchor member 100 is subject to external force "F" greater than biasing force "$F_{B1}$", seal anchor member 100 is compressed, and, once compressed, as long as external force "F" at least equals biasing force "$F_{B1}$", seal anchor member 100 remains in the compressed condition. Upon the removal of external force "F" biasing force "$F_{B1}$" acts to return seal anchor member 100 towards the expanded condition.

Figure 4:
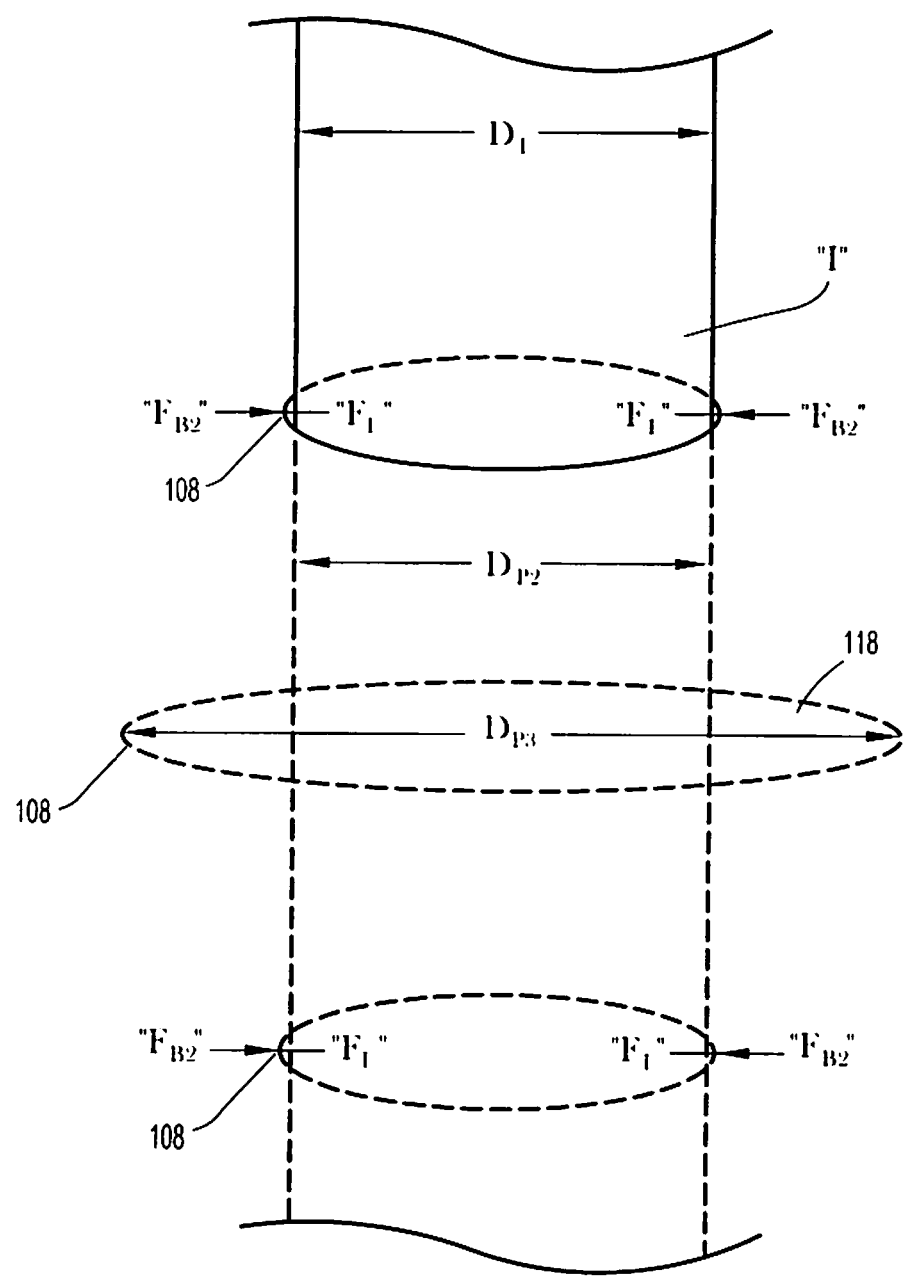
FIG. 4 is a side, schematic view of a port of the seal anchor member of FIG. 2 with a surgical object inserted therethrough.

The compressible material comprising seal anchor member 100 also facilitates the resilient transitioning of port 108 between its first stale (FIGS. 1-3) and its second state (FIG. 5). As previously discussed, prior to the insertion of surgical object "I", port 108 is in its first stale in which port 108 defines a first or initial dimension $D_{P1}$. Port 108 may incorporate a slit extending the length "L" of seal anchor member 100. In this first state, port 108 is at rest and is not subject to any external forces. However, upon the introduction of surgical object "I" through port 108 as depicted in FIG. 4, the surgical object "I" exerts a force "$F_1$" upon port 108 that is directed radially outward. Force "$F_1$" acts to enlarge the dimensions of port 108 and thereby transition port 108 into the second state thereof in which port 108 defines a second, larger dimension $D_{P2}$ that substantially approximates the diameter $D_1$ of surgical object "I". Consequently, an internal biasing force "$F_{B2}$" is created that is directed radially inward, in opposition to force "$F_1$". Internal biasing force "$F_{B2}$" endeavors to return port 108 to reduce the internal dimension of port 108 and thereby return port 108 to the first state thereof. Internal biasing force "$F_{B2}$" is exerted upon surgical object "I" and acts to create a substantially fluid-tight seal therewith. The significance of forces "$F_{B1}$" and "$F_{B2}$" will be discussed in further detail below.

Figure 6:
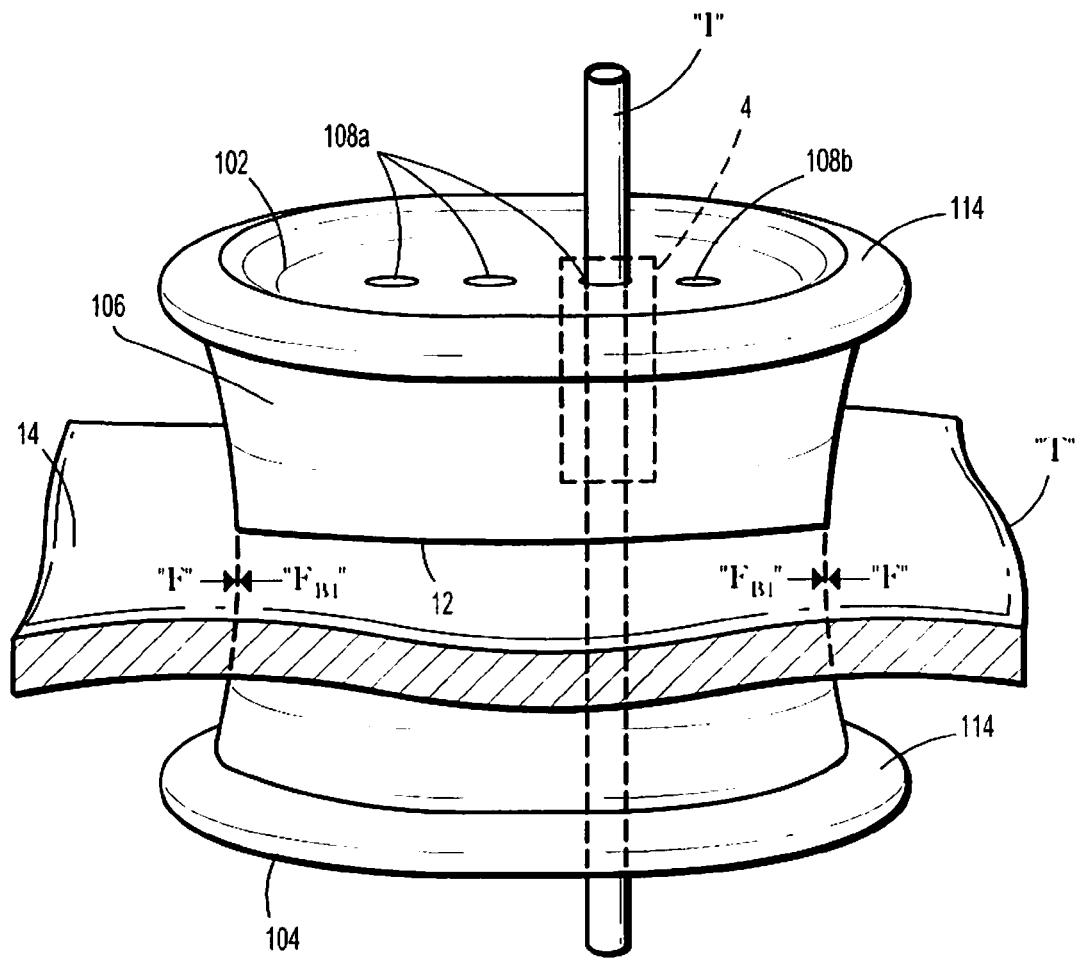
FIG. 6 is a perspective, schematic view of the seal anchor member of FIG. 1 shown in the expanded condition and subsequent to its insertion into the incision.
Figure 7:
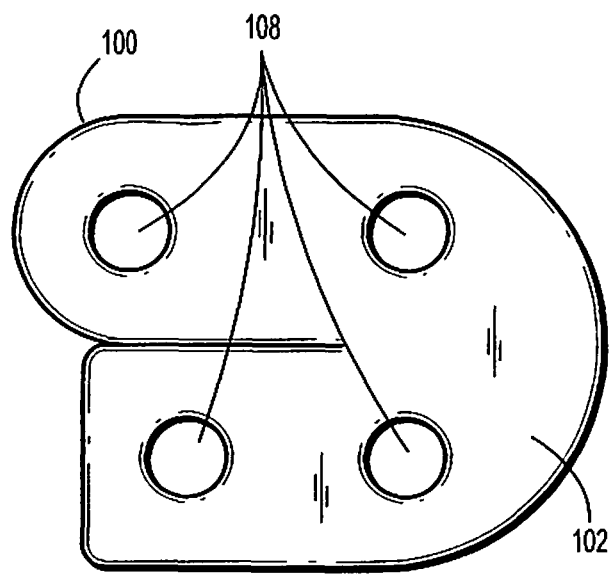
FIG. 7 is a top, plan view of the seal anchor member of FIG. 1 in a rolled state.

Referring again to FIG. 1, one or more positioning members 114 may be associated with either or both of proximal end 102 and distal end 104 of seal anchor member 100. Positioning members 114 may be composed of any suitable biocompatible material that is at least semi-resilient such that positioning members 114 may be resiliently deformed and may exhibit any suitable elongated configuration, e.g., substantially oblong or oval. Prior to the insertion of seal anchor member 100, positioning members 114 are deformed in conjunction with the respective proximal and distal ends 102, 104 of seal anchor member 100 to facilitate the advancement thereof through tissue tract 12 (FIG. 6). Subsequent to the insertion of seal anchor member 100 within tissue tract 12, the resilient nature of positioning members 114 allows positioning members to return towards their normal, e.g., substantially oblong or oval, configuration, thereby aiding in the expansion of either or both of the respective proximal and distal ends 102, 104 and facilitating the transition of seal anchor member 100 from its compressed condition to its expanded condition. Positioning members 114 also may engage the walls defining the body cavity to further facilitate securement of seal anchor member 100 within the body tissue. For example, positioning member 114 at leading end 104 may engage the internal peritoneal wall and positioning member 114 adjacent trailing end 102 may engage the outer epidermal tissue adjacent the incision 12 within tissue "T". In another embodiment of seal anchor member 100, one or more additional positioning members 114 may be associated with intermediate portion 106.

The use of seal anchor member 100 will be discussed during the course of a typical minimally invasive procedure. Initially, the peritoneal cavity (not shown) is insufflated with a suitable biocompatible gas, such as $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, a tissue tract 12 is created in tissue "T", the dimensions of which may be varied dependent upon the nature of the procedure.

Prior to the insertion of seal anchor member 100 within tissue tract 12, seal anchor member 100 is in its expanded condition in which the dimensions thereof prohibit the insertion of seal anchor member 100 into tissue tract 12. To facilitate insertion, the clinician transitions seal anchor member 100 into the compressed condition by applying a force "F" thereto, e.g., by squeezing seal anchor member 100. Force "F" acts to reduce the dimensions $D_1$ and $D_2$ of the proximal and distal ends 102, 104, respectively, to $D_1'$ and $D_2'$ (FIG. 5) including positioning members 114 (if provided) and to reduce the dimension "R" of intermediate portion 106 to "R'" such that seal anchor member 100 may be inserted into tissue tract 12. As best depicted in FIG. 6, subsequent to its insertion, distal end 104, positioning member 114 (if provided), and at least a section 112 of intermediate portion 106 are disposed beneath the tissue "T". Seal anchor member 100 is caused to transition from the compressed condition to the expanded condition by removing force "F" therefrom.

During the transition from the compressed condition to the expanded condition, the dimensions of seal anchor member 100, i.e., the respective dimensions $D_1'$, $D_2'$ (FIG. 5) of the proximal and distal ends 102, 104 are increased towards $D_1$ and $D_2$ (FIG. 6) and the dimension "R'" is increased towards "R". The expansion of distal end 104 is relatively uninhibited given the disposition thereof beneath tissue "T", and accordingly, distal end 104 is permitted to expand substantially, if not completely. However, as seen in FIG. 5, the expansion of the section 112 of the intermediate portion 106 is limited by the tissue surfaces 14 (FIG. 1) defining tissue tract 12, thereby subjecting intermediate portion 106 to an external force "F" that is directed inwardly. As discussed above, this creates an internal biasing force "$F_{B1}$" that is directed outwardly and exerted upon tissue surfaces 14, thereby creating a substantially fluid-tight seal between the seal anchor member 100 and tissue surfaces 14 and substantially inhibiting the escape of insufflation gas around seal anchor member 100 and through tissue tract 12.

In the expanded condition, the respective dimensions $D_1$, $D_2$ of the proximal and distal ends 102, 104 are larger than the dimension "R" of the intermediate portion 106. Subsequent to insertion, the dimension $D_2$ of distal end 104 and positioning member 114 is also substantially larger than the dimensions of the tissue tract 12. Consequently, seal anchor member 100 may not be removed from tissue tract 12 in the expanded condition and thus, seal anchor member 100 will remain anchored within the tissue "T" until it is returned to its compressed condition.

After successfully anchoring seal anchor member 100 within the patient's tissue "T", one or more surgical objects "I" may be inserted through ports 108. FIG. 6 illustrates a surgical object "I" introduced through one of ports 108. As previously discussed, prior to the insertion of surgical object "I", port 108 is in its first state in which port 108 defines an initial dimension $D_{P1}$ which may be negligible in that port 108, in one embodiment, is a slit. Accordingly, prior to the escape of insufflation gas through port 108, in the absence of surgical object "I" is minimal, thereby preserving the integrity of the insufflated workspace.

Surgical object "I" may be any suitable surgical instrument and, accordingly, may vary in size. Suitable surgical objects to be introduced within one or more of the ports 108 include minimally invasive grasper instruments, forceps, clip-appliers, staplers, cannula assemblies, etc. Upon the introduction of surgical object "I", port 108 is enlarged, thereby transitioning into its second state in which port 108 defines a second dimension $D_{P2}$ (FIG. 4) that substantially approximates the diameter $D_1$ of surgical object "I", thereby creating a substantially fluid-tight seal with surgical object "I" and substantially inhibiting the escape of insufflation gas (not shown) through port 108 of seal anchor member 100 in the presence of a surgical object "I", as previously discussed.

Turning now to FIGS. 8A-8D, a surgical apparatus, in accordance with an alternate embodiment of the present disclosure, is generally designated as 20. Surgical apparatus 20 is substantially identical to surgical apparatus 10 and thus will only be discussed in detail herein to the extent necessary to identify differences in construction and operation thereof.

As seen in FIG. 8A, surgical apparatus 20 comprises a seal anchor member 200 defining a plurality of ports 208, wherein the seal anchor member 200 has features that facilitate a reduction in size of the seal anchor member 200, such as by separating, e.g., cutting. Advantageously, the seal anchor member 200 is formed from a material, e.g., foam, that may be cut by a surgeon's scalpel. If seal anchor member 200 defines more ports 208 than are required for a particular surgical procedure, seal anchor member 200 may be cut to have a fewer number of ports 208. Similarly, if a surgeon desires to have a relatively smaller incision than would typically be used for the seal anchor member 200, seal anchor member 200 may be cut to reduce its, e.g., major diameter, thereby reducing the size of the incision needed to achieve optimal sealing when positioned therewithin and providing a biasing force/sealing force that is more appropriate for the smaller incision. Depending on the position of the cut to be made, cutting the seal anchor member may reduce the number of ports remaining, or the number of ports may stay the same. FIGS. 8B-8D illustrate resulting seal anchor members 210, 220, and 230 when seal anchor member 200 is cut along segment lines 8B-8B, 8C-8C, and 8D-8D respectively. Seal anchor member 200 may include indicia "I", e.g., lines or markings along segment lines 8B-8B, 8C-8C, and 8D-8D, etc., that indicate to a user a location at which to make such a cut if desired. Additionally or alternatively, the seal anchor member 200 may include, at a position that is coincident with the indicia, a weakened region "W", e.g., perforations, slits, etc., at such locations that facilitate the making of such a cut, e.g., by helping insure that a cut made at the indicia is passes through the entire seal anchor member without straying, and/or ease the making of such a cut, e.g., by reducing the effort that a surgeon might need to exert in making the cut. Seal anchor member 200 and resulting seal anchor members 210, 220, and 230, may be used in a surgical procedure in a substantially similar manner to seal anchor member 100 as discussed hereinbefore.

As set forth above, the prevent invention, according to various embodiments thereof, may provide particular advantages for. e.g., thoracic procedures (for example, thymectomies, lobectomies, pneumonectomy, esophagectomy, mediastinal tumor resection, sympathectomy, etc.) and/or single incision laparoscopic procedures in which it may be desirable to access an abdominal cavity off-midline. For example, during thoracic procedures, access is typically attained by placing cannulas or instruments between a patient's ribs. The elongated shape, when viewed in cross-section, of the seal anchor member, along with the linear arrangement of the ports therethrough, allows the seal anchor member to be inserted between a patient's ribs and to move with the natural curvature of the ribcage. In single incision laparoscopic procedures, the shape of the seal anchor member may enable it to be positioned between muscle groups, e.g., parallel to and on the lateral edge of the rectus abdominus muscles. Advantageous positioning of the seal anchor member, as described hereinabove, may provide additional benefits of reducing stretching, trauma and post-operative pain.

In some instances, thoracic procedures may not require insufflation. For other types of surgical procedures, e.g., laparoscopic procedures, insufflation may be used—for these types of procedures, the seal anchor member may be provided with insufflation tubing (not shown) or one of the ports may be specifically employed for insufflation purposes.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A seal anchor member transitionable between a compressed state and an expanded state, the seal anchor member comprising:
   a body portion including proximal and distal ends, at least one of the proximal and distal ends including an arcuate portion extending radially outward, the body portion defining a length and a pair of ports, each port of the pair of ports extending transverse to the length of the body portion between the proximal end and the distal end of the body portion, the pair of ports arranged along the length, the pair of ports adapted for sealed reception of a surgical object therethrough, the body portion including a weakened portion configured to separate a portion of the body portion to reduce the length of the body portion.

2. The seal anchor member according to claim 1, wherein the weakened portion is disposed between the pair of ports.

3. The seal anchor member according to claim 1, wherein the portion of the body portion includes one port of the pair of ports.

4. The seal anchor member according to claim 1, wherein the body portion includes indicia indicating the weakened portion.

5. The seal anchor member according to claim 1, wherein the weakened portion is one of a perforation or a slit.

6. The seal anchor member according to claim 1, wherein a length of each port of the pair of ports is independent of separation of the body portion along the weakened portion.

7. The seal anchor member according to claim 1, wherein the weakened portion is configured to separate the body portion into smaller portions independent of the surgical object located in one port of the pair of ports.

8. The seal anchor member according to claim 1, wherein the weakened portion is substantially orthogonal to the length of the body portion.

9. The seal anchor member according to claim 1, wherein the pair of ports is uniformly spaced in the body portion.

10. The seal anchor member according to claim 1, wherein the body portion has an elongated shape.

\* \* \* \* \*